United States Patent [19]

Mitsumaki et al.

[11] Patent Number: 4,680,270

[45] Date of Patent: Jul. 14, 1987

[54] METHOD AND APPARATUS FOR CONDUCTING FLOW ANALYSIS

[75] Inventors: Hiroshi Mitsumaki; Nobuyoshi Takano; Naoya Ono, all of Katsuta, Japan

[73] Assignee: Hitachi, Ltd., Tokyo, Japan

[21] Appl. No.: 509,050

[22] Filed: Jun. 29, 1983

[30] Foreign Application Priority Data

Jul. 2, 1982 [JP] Japan ............................ 57-113951

[51] Int. Cl.⁴ ...................... G01N 35/08; G01N 27/40
[52] U.S. Cl. .................................... 436/52; 204/403; 204/409; 422/68; 422/81; 422/103; 436/151; 436/74; 436/79
[58] Field of Search ................ 422/70, 81, 82, 103, 422/68; 436/52, 53, 151, 74, 79; 204/403, 409, 410

[56] References Cited

U.S. PATENT DOCUMENTS

| | | | |
|---|---|---|---|
| 3,941,659 | 3/1976 | Koch et al. | 435/291 |
| 4,022,575 | 5/1977 | Hansen et al. | 422/86 |
| 4,177,677 | 12/1979 | Ruzicka et al. | 422/82 |
| 4,272,483 | 6/1981 | Schick | 73/863.71 |
| 4,276,051 | 6/1981 | Ginsberg et al. | 422/64 |
| 4,314,824 | 2/1982 | Hansen et al. | 436/52 |
| 4,315,754 | 2/1982 | Ruzicka et al. | 422/81 |
| 4,325,910 | 4/1982 | Jordan | 422/64 |
| 4,338,279 | 7/1982 | Orimo et al. | 422/67 |
| 4,489,898 | 2/1985 | Anderson et al. | 422/74 |
| 4,536,369 | 8/1985 | Sakruda et al. | 422/64 |

Primary Examiner—Michael S. Marcus
Attorney, Agent, or Firm—Antonelli, Terry & Wands

[57] ABSTRACT

A single sampling tube is inserted into a whole blood sample contained in a sample cup, and the blood introduced into a switch-valve and a first channel without being diluted. The switch-valve has a volumetric section. In the first channel are arranged a plurality of ion-sensing electrodes, and downstream from these electrodes, a sample position sensor. The blood is led up to where the sample position sensor is located, at which point it fills the volumetric section and the ion sensing electrode channels. The sample $Na^+$, $K^+$, $Cl^-$, and $Ca^{++}$ are detected in this state. After the switch-valve switches, the flow within the volumetric section is forced towards a photometer positioned in a second channel by a reagent solution. The blood is diluted while passing through a reaction coil, during which time enzymes in the blood give rise to enzyme reactions with the reagents. The absorbance of the reaction solution is measured by the photometer.

15 Claims, 3 Drawing Figures

METHOD AND APPARATUS FOR CONDUCTING FLOW ANALYSIS

BACKGROUND OF THE INVENTION

The present invention relates to a method and apparatus for conducting flow analysis, and concerns in particular a method and apparatus capable of making a plurality of specific determinations for a single liquid sample.

Flow analyzing methods are techniques whereby a liquid sample is made to flow through a conduit to a detector, where measured values are obtained for some analytical item. One type of flow analyzing method, as exemplified by U.S. Pat. No. 4,177,677, involves reacting the sample with reagents, then leading the reacted sample to a photometer. Another type of flow analyzing method, U.S. Pat. No. 4,452,682, consists of leading an undiluted sample to a detector, where it is analyzed.

It has heretofore been necessary, when conducting both assays involving dilution of the sample and assays that do not involve sample dilution, to use at least two analyzers. This means that when the assay conditions differ for the respective tests, it has been necessary to supply discreet blood samples separately to each of the analyzers. The additional requirement of a washing step in each of the analyzers in order to prevent sample cross-contamination has necessitated the use of a large amount of sample.

SUMMARY OF THE INVENTION

One object of the present invention is to provide an analytic method and apparatus for liquid samples that allows a plurality of specific determinations requiring different assay conditions to be carried out with a single flow analyzer.

Another object of the present invention is to provide an analytic method and apparatus that consumes only a very small amount of sample, in spite of the ability to make a plurality of different determinations.

In the present invention, a first and second channel are connected to a switch-valve having a volumetric section. When liquid sample is introduced into the first channel, the sample is held such that a sample segment extends through both the first channel and the volumetric section. Specific assays are conducted, without dilution, on the sample portion present in the first channel by means of a first detector. The portion of the sample cut off by the volumetric section is introduced together with a diluent into the second channel, where it is diluted, and other assays carried out by the second detector.

BRIEF DESCRIPTION OF THE DRAWINGS

The present invention will be more clearly understood from the detailed description set forth below, considered in conjunction with the figures accompanying and forming a part of the specification, in which.

DETAILED DESCRIPTION OF THE PREFERRED EMBODIMENTS

Figure 1:
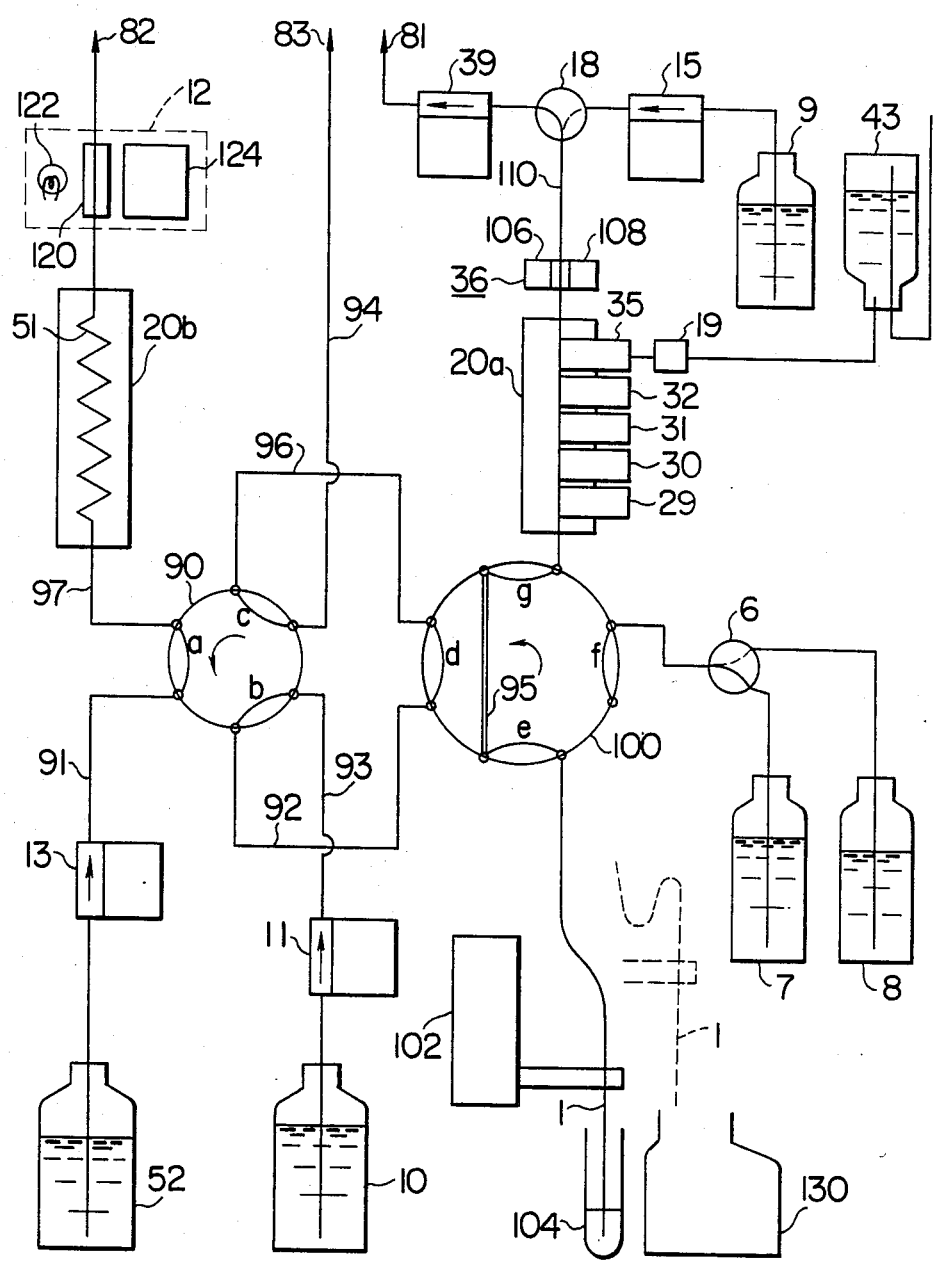
FIG. 1 is a schematic flow diagram of one embodiment of the present invention.

FIG. 1 shows an embodiment of the present invention consisting of a flow analyzer equipped with a plurality of ion-sensing electrodes and a photometer for the measurement of a chemically reacted solution. A sampling tube 1 is connected to a flow switching valve 100. This tube 1 ascends and descends by means of a vertical nozzle movement mechanism 102, at the same time as which it moves toward the position shown by the dashed lines above a waste container. Ion-selective electrodes 29, 30, 31, and 32 for measuring sodium ions, potassium ions, chloride ions, and calcium ions, respectively, are arranged in parallel along a first channel 110 connected to flow switching valve 100, as are also a reference electrode 35, a liquid sensor 36, a three-way switch-valve 18, and a peristaltic liquid feed pump 39. The ion-selective electrodes are arranged in a manner such as to expose the sensing membranes to a section of the channel lying near switch-valve 100, and the vicinity of the channel maintained at a predetermined temperature by means of a constant-temperature jacket 20a.

The second channel includes a conduit 96, a switch-valve 90, and a conduit 97. A portion of conduit 97 is formed as a reaction coil 51. Conduit 97 passes through a flow cell 120 of a photometer 12. Flow cell 120 is irradiated with light from a light source 122; after passing through flow cell 120, the light is split into different wavelengths by a spectroscope 124, and received as a variety of monochromatic light components. Signals consisting of monochromatic light at wavelengths suited to the specific assays to be conducted are processed with a microprocessor (not shown). The length of the second channel from switch-valve 100 to the photometer 12 is much greater than the length of the first channel from switch valve 100 to the electrodes. The reaction coil is maintained at a predetermined temperature by a constant temperature jacket 20b.

As is clear from the diagram, rotary valves are used as switch-valves 90 and 100, but a similar action may be obtained with slide-valves as well. Rotary valves 90 and 100 can be rotated counterclockwise one port at a time. Valve 90 is provided with connector passages, a, b, and c, while valve 100 is provided with connector passages d, e, f and g. These connector passages are all movable. In addition, valve 100 is provided with a cavity or compartment having a given volume. A switch-valve 6 connected to channel switch-valve 100 selects either container 7 or 8, which hold standard solutions at different concentrations.

A peristaltic pump 15 feeds a washing fluid in a container 9 in the direction opposite to the normal flow, passing it successively through conduit 110, volumetric compartment 95, and sampling tube 1, then discharging it into waste container 130. Peristaltic pump 11 feeds a reagent solution stored in a container 10, and peristaltic pump 13 feeds a carrier solution consisting of distilled water stored in a container 52. Reference numerals 81, 82, and 83 represent drains.

Liquid sensor 36, which is positioned downstream from the specific-ion electrodes, includes a light source 106 and a photodetector 108 arranged opposite each other on either side of conduit 110. An electrode solution held in a container 43 is supplied to reference electrode 35 through a control valve 19.

The operation of the present embodiment shall now be described. All moving elements of the analyzer are controlled by a microprocessor-equipped control unit.

Step 1

When a sample cup 104 containing a sample of whole blood to which a small amount of anticoagulant has been added is placed at a predetermined position, the vertical nozzle movement mechanism is actuated, causing the sampling tube 1 to descend. At this point, the analyzer channels are arranged as shown in the drawing, such that the carrier solution flows through conduit 91, connector passage a, conduit 97, and flow cell 120. The reagent solution fed by peristaltic pump 11 flows through conduit 93, connector passage b, conduit 92, connector passage d, conduit 96, connector passage c, and conduit 94 before being discharged. Conduits 92 and 96, which are tubes of fixed volumetric capacities, are already at this point filled with the reagent solution. When tube 1 is inserted into the blood sample, this activates peristaltic pump 39, which then aspirates through tube 1 a volume of blood greater than the sum total of the capacities of the volumetric compartment and the conduit along which the ion-sensing electrodes are arranged. The blood is transferred to liquid sensor 36 through connector passage e, volumetric compartment 95, and connector passage g. The blood sample within the conduit is segmented from a transparent standard solution or the washing fluid by air bubbles.

Step 2

When the leading end of the whole blood sample preceded by an air bubble reaches liquid sensor 36, the presence of the blood is detected and pump 39 shut off, at which point the blood sample extends from liquid sensor 36 to the lower end of sampling tube 1. Next, the vertical nozzle movement mechanism 102 is actuated, and sampling tube 1 raised. Following this, the blood segment is drawn upwards by the action of pump 39 until the trailing end is just short of channel switch-valve 100, at which point pump 39 is turned off. The blood segment, which remains uncontaminated, is now in direct contact with all the ion-selective electrodes and the reference electrode 35, which together comprise the first detector means, and moreover, is present in volumetric compartment 95. The ion-selective electrodes now begin to measure the various ion concentrations, in this case, $Na^+$, $K^+$, $Cl^-$, and $Ca^{2+}$. Ion concentrations are thus measured without dilution of the sample.

Step 3

Figure 2:
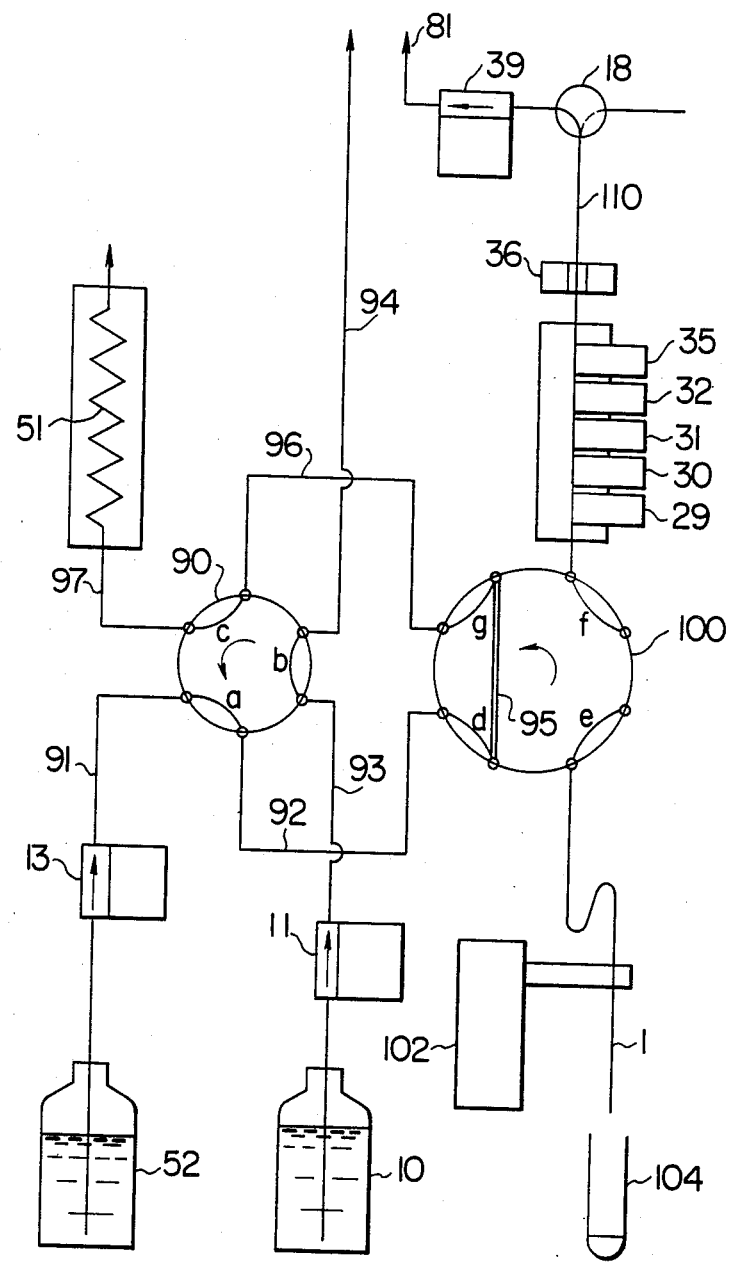
FIG. 2 is a schematic flow diagram of the embodiment of FIG. 1, but with the conduit switched.

Channel switching valves 100 and 90 are then each rotated one port to give the arrangement shown in FIG. 2. The carrier solution is introduced to conduit 97 via conduit 91, connector passage a, conduit 92, connector passage d, volumetric compartment 95, connector passage g, conduit 96, and connector passage c. The blood sample held in volumetric compartment 95 is forced out by the carrier solution while remaining trapped on both ends between the reagent solution, and made to enter conduit 97. As the blood sample passes through the long reaction coil 51, it becomes diluted by the reagent solution and the carrier solution, causing the reaction between the sample and the reagents to proceed gradually. While this is happening, pump 39 shuts off, the ion concentration determinations carried out, and the results output by a printer (not shown). Once this is done, the sample is discharged by pump 39 from drain 81.

Step 4

Switch-valve 100 is rotated one step from the position in FIG. 2, and sampling tube 1 moved over waste container 130, such that it communicates with connector channel d, volumetric compartment 95, connector channel f, and conduit 110, at which time pump 39 shuts off. Switch-pump 18 is switched to the position shown by the dotted line, and peristaltic pump 15 actuated. This causes the washing fluid to be discharged from sampling tube 1 into waste container 130 via conduit 110 and volumetric compartment 95.

While this is happening, the solution of sample and reagent that has reacted within reaction coil 51 is introduced into the flow cell 120 associated with the photometer 12, where the color is quantitatively measured and the concentrations of the substances being assayed determined. A variety of determinations, such as GOT, GPT, creatinine, amidase, glucose, and total protein, can be made by the appropriate selection of the reagents used.

Step 5

Switching valves 90 and 100 are both rotated one step, and conduit 97 and flow cell 120 flushed with the carrier solution. Switch-valve 18 is then rotated back to the position shown by the solid line, and pump 39 actuated. The standard solution selected by switch-valve 6 flows through connector channel e into channel 110, washing it in the process. As this is happening, sampling tube 1 is returned by vertical nozzle movement mechanism 102 back to the sampling position.

Step 6

Switch-valve 100 is rotated one step and pump 39 shut off. Sampling tube 1 now communicates with connector passage g, volumetric compartment 95, connector passage e, and conduit 110. Peristaltic pump 11, which had been shut off, is actuated, then once again shut off when conduits 92 and 96 become filled with the reagent solution. At this point, the reagent circuit consists of conduit 93, connector passage a, conduit 92, connector passage f, conduit 96, connector passage b, and conduit 94. Following this, the analyzer awaits the arrival of the next blood sample. When the next sample is placed in the sampling position, the operations in steps 1 through 6 above are repeated as before.

According to the embodiment in FIG. 1, both determinations by ion-selective electrode (ISE) ($Na^+$, $K^+$, $Cl^-$, and $Ca^{++}$) procedures in which the blood sample is not diluted and by analytic procedures involving the measurement of a reaction solution obtained by the dilution of blood with reactive reagents can be performed easily and rapidly merely by aspirating a whole blood sample with a single sampling nozzle. In addition, the amount of blood is kept to an absolute minimum (in this embodiment, 120 $\mu$l), and because all the sensing terminals are linked by tubing, there is no need for samplers that sample and partition blood, making it possible to simplify and scale down the size of the analyzer, simplified and reduced in size.

Figure 3:
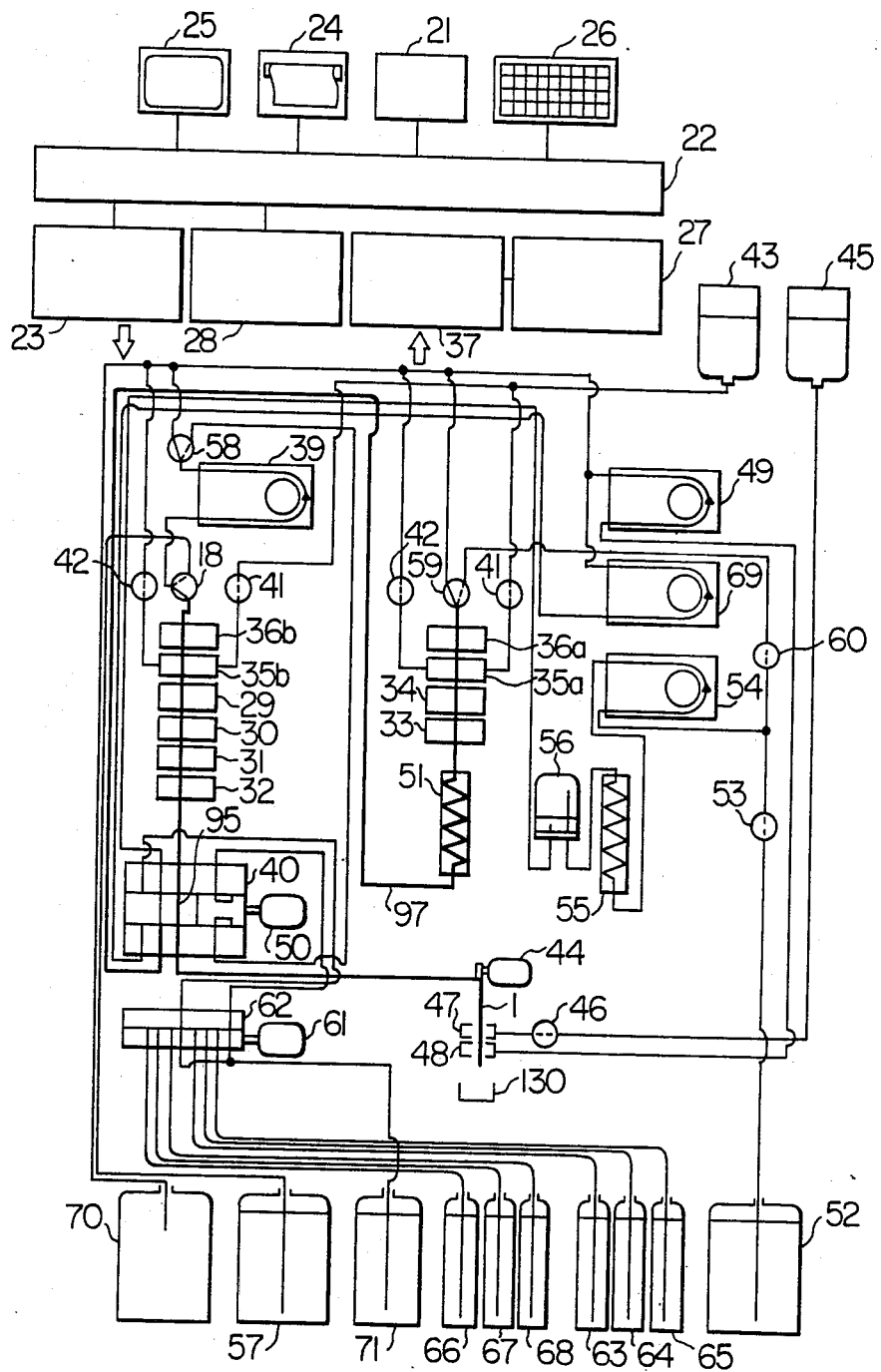
FIG. 3 is a schematic flow diagram of another embodiment of the present invention.

FIG. 3 is a schematic flow diagram of another embodiment. In this example, using whole blood as the sample, determinations such as $Na^+$, $K^+$, $Cl^-$, done on undiluted samples were conducted in parallel with urea, blood sugar, and other determinations that involve sample dilution. This combination of assays consists of: (1) substances (electrolytes) such as $Na^+$, $K^+$, and $Cl^-$ quantitatively determined by the direct measurement of blood with ISE's; (2) substances such as urea and blood sugar determined by mixing a fixed amount of blood with an enzyme-containing reactive reagent and quantitatively measuring the products of the reaction with ISE's or polarographic electrodes, i.e., substances (metabolic components) involving the analysis of blood diluted with a reactive reagent; and (3) substances such as GOT and GPT determined by mixing a fixed amount of blood with a reaction solution containing substrate and quantitatively measuring the resulting products with ISE's or polarographic electrodes. Other substances that fall within the above categories are also applicable here, these by no means being limited only to $Na^+$, $K^+$, $Cl^-$, urea, and blood sugar.

The analyzing apparatus in FIG. 3 is comprised of two basic systems: a flow analyzing conduit system and a control system. The pumps, valves, and motors included in the flow analyzing conduit system are all driven by signals transmitted via an interface 22 and a driver 23 under commands issued by a microcomputer in the control system. In addition to the microcomputer 21 just mentioned, a printer 24, a CRT display 25, a keyboard panel 26, an analog-digital converter 27, and a comparator 28 are also linked together in the control system through interfaces. Signals from a sodium electrode 29, a potassium electrode 30, a chloride electrode 31, a calcium electrode 32, a glucose-measuring immobilized enzyme electrode 33, a urea-measuring immobilized enzyme electrode 34, and reference electrodes 35a and 35b are input to the analog digital converter via a preamplifier 37. Signals from a liquid sensor 36 are input to the microcomputer 21 via the comparator 28.

The elements making up the flow analyzing conduit system shall now be described in the order in which they participate in the analytical procedure. Using a squeeze pump 39, a blood sample is led from a nozzle 1 through a cut valve 40 to a measuring chamber in which are provided a sodium electrode 29, a calcium electrode 30, a chloride electrode 31, and a calcium electrode 32. The apparatus is designed such that a reference electrode solution 43 flows into reference electrode 35a and 35b via two control valves, 41 and 42, to form a suitable liquid junction. The blood sample that has been introduced is detected by liquid sensor 36, and the completion of sample entry displayed on the keyboard panel 26. The sampling nozzle 1 is lowered by a pulse motor 44. The outside surface of nozzle 1 is washed in washing tank 47 by being sprayed with distilled water under the control of valve 46, and the waste water drained off by aspiration from waste container 48 by pump 49. The trailing end of the blood sample is then transferred by the action of pump 39 to the vicinity of the pump 40 inlet and stopped. At the cut pump 40, a slide valve disposed between a pair of fixed valves is driven by motor 50, and the volumetric blood cut portion 95 at the center of the cut pump transferred to the reaction coil 51, glucose electrode 33, and urea electrode 34 channels. Carrier solution 52 is fed via valve 53 to conduit 97 by means of a pump 54; it flows through a carrier solution heating coil 55 and a damper 56, while the blood cut portion flows toward the reaction coil and is expanded within conduit 97. 36a is a liquid sensor.

These conduits that come into contact with the blood samples may be washed when desired with physiological saline solution 57 through the adjustment of valves 58 and 59. While awaiting a blood sample, a circulating flow circuit can be formed for the carrier solution by the adjustment of valves 53 and 60 to give a low carrier solution consumption. Calibration of each of the electrodes is carried out by introducing standard solution into the respective electrode conduits via a switch-valve 62 driven by a motor 61. Three standard solutions 63, 64, and 65 for the sodium, potassium, chloride, and calcium electrodes are successively introduced under the action of pump 39 through the control of switch-valve 62 and cut valve 40. Three standard solutions 66, 67, and 68 for the glucose and urea electrodes are synchronized with the above switch-valve and cut valve and introduced into the cut valve under the action of a pump 69. Sodium, potassium, chloride, and calcium determinations for the blood and standard solutions are carried out by potentiometric measurements a fixed time after the sample has stopped at the electrodes. Glucose and urea determinations are carried out with electrodes equipped with immobilized enzyme membranes; what is actually measured here are the peak heights of the blood cut segments expanded with the carrier solution. The glucose is measured polarographically, and the urea, potentiometrically.

The results measured for the blood samples are converted into concentrations using the parameters stored in the microcomputer 21 during measurement of the standard solutions. These results are output on a printer 24 and at the same time displayed on a CRT display 25. The blood samples, standard solution, carrier solution, physiological saline solution, and distilled water are all stored in discharge tank 70 following determinations. The washing fluid 71 is led to a conduit by the same inlet system as that used by the standard solutions, and the conduits contaminated by the blood samples washed. The fluid back-flushed through nozzle 1 is received by discharge plate 130.

It is therefore possible, in the above-described manner, to take up both samples to be diluted and samples not to be diluted with a single aspiratory operation using just one nozzle, and to reduce the sample needed for a number of different determinations to a very small quantity. Moreover, in the case of liquid samples introduced through a single sample inlet port in flow-type analyzers, the apparatus described has the ability to monitor a portion of the sample that has been stopped for a predetermined time without adding reagent, and to add reagent to another portion to dilute and react it, and cause it to flow while making different determinations.

As described above, according to the present invention, samples can be drawn and correctly processed through a single sampling operation for a number of individual determinations requiring different treatment conditions, making the present invention highly effective for minimizing the quantity of sample consumed.

What is claimed is:

1. A method of flow analysis using a switch-valve having a volumetric section and a first analytical detector with at least one ion selective electrode, comprising the steps of:
   communicating said volumetric section and said first detector,
   aspirating an undiluted liquid sample through conduits in both said volumetric section and said first detector,
   switching said switch-valve to force out the undiluted sample within said volumetric section with a diluent, diluting said sample with said diluent while transferring said sample and introducing it into a second detector for analytic determinations; and obtaining one type of determination for an undiluted sample from said first detector and also obtaining a different determination for a diluted sample from said second detector.

2. A flow analyzing method according to claim 1 wherein said diluent is a reagent solution.

3. A flow analyzing method according to claim 1 including the further step of causing a washing fluid to flow, in said conduits within said first detector and in said volumetric section, in a direction opposite to that of sample aspiration.

4. A method for flow analysis, comprising: communicating a volumetric section provided on a switch valve with a sampling tube and a first flow cell;

distributing a blood sample aspirated through the sampling tube without dilution to both the volumetric section and the first flow cell;

switching the valve, thereby pushing the sample out of the volumetric section by means of a carrier liquid and transferring the sample to a second flow cell;

measuring the sample in the first flow cell by means of a first detector;

diluting the sample with a diluent while transferring the sample from the volumetric section to the second cell; and measuring the diluted sample in the second flow cell by means of a second detector.

5. A method according to claim 4, including a further step of washing the inside of the first flow cell with a washing liquid and then passing a standard solution through the first flow cell.

6. A method according to claim 4, wherein the measurement in the first flow cell is of an undiluted sample to obtain at least one determination; and the measurement in the second flow cell is to obtain at least one determination different from the at least one determination obtained by measuring the undiluted sample.

7. A method for flow analysis, comprising:

filling a reagent volumetric section with a reagent solution;

communicating a sample volumetric section provided on a switch valve with a sampling tube and a first flow cell;

distributing a blood sample aspirated through the sampling tube without dilution to both the sample volumetric section and the first flow cell;

switching the valve, thereby transferring the sample out of the sample volumetric section and the reagent solution from the reagent volumetric section to a second flow cell;

measuring the sample in the first flow cell by means of a first detector;

mixing the sample with the reagent solution, while transferring the sample from the sample volumetric section to the second flow cell; and measuring the reaction solution of the sample and the reagent solution in the second flow cell by means of a second detector.

8. A method according to claim 7, wherein the measurement in the first flow cell is of an undiluted sample to obtain at least one determination; and the measurement in the second flow cell is to obtain at least one determination different form the at least one determination obtained by measuring the undiluted sample.

9. A method for flow analysis using a flow analyzer provided with a first flow cell provided near a switch-valve having a volumetric compartment and a second flow cell provided at the switch valve through a reaction coil, and with a single intake tube connected to the switch valve comprising the steps of:

inserting the intake tube into a sample cup containing a blood sample, and intaking the blood sample towards the switch-valve through the intake tube by suction;

distributing the sample in an undiluted state into the volumetric compartment and the first cell while the volumetric compartment and the first flow cell communicate with each other;

switching the switch valve to shut the volumetric compartment off from the first flow cell, and then pushing the sample in the volumetric compartment towards the reaction coil by means of a carrier liquid;

diluting the sample in the reaction coil with the carrier liquid and then leading the diluted sample to the second flow cell; and measuring a first analytical item in the sample in the undiluted state in the first flow cell by a first detector, and measuring a second analytical item different from said first analytical item in the diluted sample in the second flow cell by a second detector.

10. A method according to claim 9, wherein the first detector is an ion selective electrode and the second detector is a photometer.

11. A method according to claim 9, wherein the first detector is an ion selective electrode, and the second detector is an immobilized enzyme electrode.

12. A method according to claim 9, wherein the carrier liquid is a reagent solution.

13. A method for flow analysis using a flow analyzer provided with a first flow cell provided near a switch-valve having a volumetric compartment and a second flow cell provided at the switch valve through a reaction coil, and with a single intake tube connected to the switch valve comprising the steps of:

inserting the intake tube into a sample cup containing a blood sample, and intaking the blood sample towards the switch-valve through the intake tube by suction;

distributing the sample in an undiluted state into the volumetric compartment and the first cell while the volumetric compartment and the first flow cell communicate with each other;

switching the switch-valve to shut the volumetric compartment off from the first flow cell, and then pushing the sample in the volumetric compartment towards the reaction coil by means of a carrier liquid;

diluting the sample in the reaction coil with the carrier liquid and then leading the diluted sample to the second flow cell;

measuring a concentration of ions in the sample in the undiluted state in the first flow cell by an ion selective electrode while keeping the sample in a standstill state; and measuring a different analytical item: in the diluted sample led in the second flow cell by a photometer or an immobilized enzyme electrode.

14. A method according to claim 13, wherein the diluted sample in the second flow cell is measured while being in a flowing state through the second flow cell.

15. A method for flow analysis using a flow analyzer provided with a first flow cell provided near a switch-valve having a volumetric compartment and a second flow cell provided at the switch valve through a conduit, and with a single intake tube connected to the switch valve;

inserting the intake tube into a sample cup containing a blood sample, and intaking the blood sample towards the switch-valve through the intake tube by suction;

detecting the forward end of the sample having passed through the volumetric compartment, thereby discontinuing the suction-intaking motion;

separating the intake tube from the sample in the sample cup during the discontinuation of the suction-intaking action;

then, moving the sample retained in the intake tube, thereby distributing the sample in an undiluted state into the volumetric compartment and the first flow cell;

switching the switch-valve to shut the volumetric compartment off from the first flow cell, and then pushing the sample in the volumetric compartment towards the conduit by means of a carrier liquid;

diluting the sample in the conduit with the carrier liquid and then leading the diluted sample to the second flow cell; and measuring a first analytical item in the sample in the undiluted state in the first flow cell by a first detector, and measuring a second analytical item in the diluted sample different from the first analytical item in the second flow cell by a second detector.

\* \* \* \* \*